(12) United States Patent
Dai et al.

(10) Patent No.: US 11,620,763 B2
(45) Date of Patent: Apr. 4, 2023

(54) METHOD AND DEVICE FOR RECOGNIZING FUNDUS IMAGE, AND EQUIPMENT

(71) Applicant: BEIJING ZHENHEALTH TECHNOLOGY CO., LTD., Beijing (CN)

(72) Inventors: Liming Dai, Beijing (CN); Hongyang Jiang, Beijing (CN); Zhanbo Yang, Beijing (CN); Dongdong Zhang, Beijing (CN)

(73) Assignee: BEIJING ZHENHEALTH TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 17/633,162

(22) PCT Filed: Aug. 17, 2021

(86) PCT No.: PCT/CN2021/112938
§ 371 (c)(1),
(2) Date: Feb. 4, 2022

(87) PCT Pub. No.: WO2022/088856
PCT Pub. Date: May 5, 2022

(65) Prior Publication Data
US 2022/0319036 A1 Oct. 6, 2022

(30) Foreign Application Priority Data
Oct. 28, 2020 (CN) .......................... 202011173393.8

(51) Int. Cl.
*G06T 7/13* (2017.01)
*G06V 40/18* (2022.01)
(Continued)

(52) U.S. Cl.
CPC .............. *G06T 7/70* (2017.01); *A61B 5/7267* (2013.01); *A61B 5/7275* (2013.01); *G06T 3/40* (2013.01);
(Continued)

(58) Field of Classification Search
CPC ........... G06T 7/70; G06T 3/40; G06T 7/0012; G06T 7/11; G06T 7/13; G06T 7/60;
(Continued)

(56) References Cited

U.S. PATENT DOCUMENTS

2009/0268159 A1  10/2009  Xu et al.
2012/0230564 A1* 9/2012  Liu ...................... A61B 3/0025
                                                   382/128
(Continued)

FOREIGN PATENT DOCUMENTS

CN   106408564 A   2/2017
CN   107292868 A   10/2017
(Continued)

OTHER PUBLICATIONS

Wang et al. "Ellipse Detection of Optic Disc-and-Cup Boundary in Fundus Images." 16th International Symposium on Biomedical Imaging, Apr. 8, 2019, pp. 601-604 (Year: 2019).*
(Continued)

*Primary Examiner* — Jon Chang (57) ABSTRACT

The present disclosure relates to a method and device for recognizing a fundus image, and equipment. The method includes: obtaining an acquired fundus image, and pre-processing the acquired fundus image; inputting the pre-processed fundus image to a trained optic disc (OD) prediction model, and performing OD prediction on the fundus image by the OD prediction model to obtain a corresponding OD prediction map, where the OD prediction map is marked with one or more located candidate areas of the OD; and
(Continued)

obtaining the OD prediction map and performing ellipse fitting to obtain ellipse fitting parameters of the candidate areas of the OD, and determining an OD area in the fundus image based on the number of the candidate areas of the OD and the ellipse fitting parameters.

12 Claims, 7 Drawing Sheets

(51) Int. Cl.
    *G06V 10/22*     (2022.01)
    *G06T 7/00*     (2017.01)
    *G06V 10/25*     (2022.01)
    *G06T 7/70*     (2017.01)
    *G06T 7/11*     (2017.01)
    *A61B 5/00*     (2006.01)
    *G06T 3/40*     (2006.01)
    *G06T 7/60*     (2017.01)

(52) U.S. Cl.
    CPC .............. *G06T 7/0012* (2013.01); *G06T 7/11* (2017.01); *G06T 7/13* (2017.01); *G06T 7/60* (2013.01); *G06V 10/22* (2022.01); *G06V 40/193* (2022.01); *G06T 2207/20081* (2013.01); *G06T 2207/30041* (2013.01); *G06V 10/25* (2022.01); *G06V 2201/03* (2022.01)

(58) Field of Classification Search
    CPC . G06T 2207/20081; G06T 2207/30041; G06T 2207/20084; A61B 5/7267; A61B 5/7275; G06V 10/22; G06V 40/193; G06V 2201/03; G06V 10/25
    See application file for complete search history.

(56) References Cited

U.S. PATENT DOCUMENTS

2020/0260944 A1    8/2020    Sun et al.
2022/0058796 A1*    2/2022    Vaghefi Rezaei ..... G06T 7/0012

FOREIGN PATENT DOCUMENTS

| CN | 108416344 A | | 8/2018 | |
|---|---|---|---|---|
| CN | 108520522 A | * | 9/2018 | ............... G06T 7/11 |
| CN | 108961280 A | | 12/2018 | |
| CN | 109472781 A | | 3/2019 | |
| CN | 109829877 A | | 5/2019 | |
| CN | 110298850 A | | 10/2019 | |
| CN | 112001920 A | | 11/2020 | |
| WO | 2019083129 A1 | | 5/2019 | |

OTHER PUBLICATIONS

Jiang et al. "JointRCNN: A Region-Based Convolutional Neural Network for Optic Disc and Cup Segmentation." IEEE Transactions on Biomedical Engineering, vol. 67, No. 2, Feb. 2020, pp. 335-343 (Year: 2020).*
Alghmdi et al. "Measurement of Optical Cup-to-Disc Ratio in Fundus Images for Glaucoma Screening." International Workshop on Computational Intelligence for Multimedia Understanding, Oct. 29, 2015, 5 pages (Year: 2015).*
Sun et al. "Optic Disc Segmentation from Retinal Fundus Images via Deep Object Detection Networks." 40th Annual International Conference of the IEEE Engineering in Medicine and Biology Society, Jul. 18, 2018, pp. 5954-5957 (Year: 2018).*
Jiang et al. "Optic Disc and Cup Segmentation with Blood Vessel Removal from Fundus Images for Glaucoma Detection." 40th Annual International Conference of the IEEE Engineering in Medicine and Biology Society, Jul. 18, 2018, pp. 862-865 (Year: 2018).*
English Translation of CN108520522A (Year: 2018).*
International Search Report and Written Opinion, PCT/CN2021/112938, dated Nov. 18, 2021, 5 pages.

* cited by examiner

METHOD AND DEVICE FOR RECOGNIZING FUNDUS IMAGE, AND EQUIPMENT

CROSS REFERENCE TO RELATED APPLICATION

This is a U.S. National Stage Application under 35 U.S.C. 371 of PCT Application No. PCT/CN2021/112938, filed Aug. 17, 2021, which claims priority to Chinese Application No. 202011173393.8, filed Oct. 28, 2020, each of which are hereby incorporated by reference in their entirety.

TECHNICAL FIELD

The present disclosure relates to the field of image processing, and in particular to a method and device for recognizing a fundus image, and equipment.

BACKGROUND ART

In recent years, with the continuous development of machine learning, especially deep learning, as well as the continuous improvement of medical imaging acquisition equipment, more and more researchers are devoted to the field of artificial intelligence medicine, which has made significant progress in medical image processing. According to an optic disc (OD) and optic cup (OC) positioning algorithm based on deep learning, enough training data is acquired to train a deep learning model to automatically learn characteristics of an OD area. However, since deep learning is data-driven, and currently disclosed data sets are desktop images, the OD area is relatively obvious. When the actually photographed fundus images have abnormalities such as light leakage, rainbow spots, and lens stains due to the influence of the shooting equipment and shooting methods, multiple candidate areas of the OD and the OC will often appear when the OD and the OC are recognized based on deep learning, thereby affecting the accuracy of detection results of the OD.

SUMMARY

Based on this, it is necessary to provide a method and device for recognizing a fundus image, and equipment, which can effectively improve the accuracy of detection results of the OD.

To implement the above objective, the present disclosure provides the following solutions:

According to one aspect of the present disclosure, a method for recognizing a fundus image is provided, including:

obtaining an acquired fundus image, and pre-processing the acquired fundus image;

inputting the pre-processed fundus image to a trained OD prediction model, and performing OD prediction on the fundus image by the OD prediction model to obtain a corresponding OD prediction map, wherein the OD prediction map is marked with one or more located candidate areas of an OD; and obtaining the OD prediction map and performing ellipse fitting to obtain ellipse fitting parameters of the candidate areas of the OD in the OD prediction map, and determining an OD area in the fundus image based on the number of the candidate areas of the OD and the ellipse fitting parameters.

In a possible implementation, a process of determining an OD area in the fundus image based on the number of the candidate areas of the OD and the ellipse fitting parameters may include:

when there are two or more candidate areas of the OD, according to the ellipse fitting parameters corresponding to each candidate area of the OD, cropping a corresponding elliptic area from the OD prediction map;

performing edge detection on each elliptic area to obtain a vascular pixel map of each candidate area of the OD; and calculating the number of vascular pixels in each vascular pixel map, and determining the final OD area according to the number of vascular pixels.

In a possible implementation, a process of determining the final OD area according to the number of vascular pixels may include:

selecting the candidate area of the OD with the largest number of vascular pixels as the OD area.

In a possible implementation, when edge detection is performed on each elliptic area, a multi-level edge detection algorithm based on a Canny operator may be used for detection.

In a possible implementation, a process of obtaining the OD prediction map and performing ellipse fitting may include:

performing binarization processing on the OD prediction map, and converting the OD prediction map into a binary map, and performing the ellipse fitting on the candidate areas of the OD in the binary map to obtain the corresponding ellipse fitting parameters.

In a possible implementation, the method may further include a step of recognizing an OC:

obtaining a partial image of the OD with a center of the OD as an image center, inputting the partial image of the OD into a trained OC prediction model, and performing OC prediction on the partial image of the OD by the OC prediction model to obtain a candidate area of the OC;

performing ellipse fitting on the candidate area of the OC, and determining a relationship between a boundary of the candidate area of the OC and the OD area according to fitting results; and when it is determined that the boundary of the candidate area of the OC exceeds the OD area, adjusting the candidate area of the OC until the adjusted candidate area of the OC is within the OD area so as to determine the position of the OC.

In a possible implementation, when the candidate area of the OC is adjusted, the mask Otsu threshold method may be used to adjust the candidate area of the OC by using the partial image of the OD as a mask.

In a possible implementation, when the candidate area of the OC is adjusted, the method may further include:

determining whether the current adjustment is the first adjustment;

when the current adjustment is the first adjustment, expanding the candidate area of the OC as the candidate area of the OC to be adjusted; and when the current adjustment is not the first adjustment, reducing the candidate area of the OC as the candidate area of the OC to be adjusted.

According to another aspect of the present disclosure, a device for recognizing a fundus image is further provided, including: an image pre-processing module, an OD positioning module, an ellipse fitting module, and an OD area determining module.

The image pre-processing module is configured to obtain an acquired fundus image, and pre-process the acquired fundus image.

The OD positioning module is configured to input the pre-processed fundus image to a trained OD prediction model, and perform OD prediction on the fundus image by the OD prediction model to obtain a corresponding OD prediction map. The OD prediction map is marked with one or more located candidate areas of the OD.

The ellipse fitting module is configured to obtain the OD prediction map and perform ellipse fitting to obtain ellipse fitting parameters of the candidate areas of the OD in the OD prediction map.

The OD area determining module is configured to determine an OD area in the fundus image based on the number of the candidate areas of the OD and the ellipse fitting parameters.

According to another aspect of the present disclosure, equipment for recognizing an OD in a fundus image is further provided, including:

a processor; and a memory, configured to store an instruction executable by the processor, where the processor is configured to implement any one of the above methods when executing the executable instruction.

According to the method for recognizing a fundus image of the embodiment of the present disclosure, the trained OD prediction model is used for positioning of the OD in the fundus image, the candidate areas of the OD are first located in the fundus image, then ellipse fitting is performed on the located candidate areas of the OD, and then the final OD area is determined according to the number of the candidate areas of the OD and the ellipse fitting parameters. Therefore, for the acquired fundus images with low imaging quality (that is, fundus images with light leakage, rainbow spots, and lens stains), multiple possible candidate areas of the OD can still be located from the fundus image by the OD prediction module, and then the final OD area is selected and determined from the multiple candidate areas of the OD, which not only realizes recognition and positioning of the OD area of the fundus image in various situations, but also effectively improves the accuracy of the positioning of the OD area.

BRIEF DESCRIPTION OF THE DRAWINGS

To describe the technical solutions in embodiments of the present disclosure or in the prior art more clearly, the accompanying drawings required in the embodiments will be briefly described below. Apparently, the accompanying drawings in the following description show merely some embodiments of the present disclosure, and other drawings can be derived from these accompanying drawings by those of ordinary skill in the art without creative efforts.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments obtained by those of ordinary skill in the art on the basis of the embodiments of the present disclosure without creative efforts shall fall within the protection scope of the present disclosure.

To make the above objectives, features, and advantages of the present disclosure clearer and more comprehensible, the present disclosure will be further described in detail below with reference to the accompanying drawings and the specific implementations.

Figure 1:
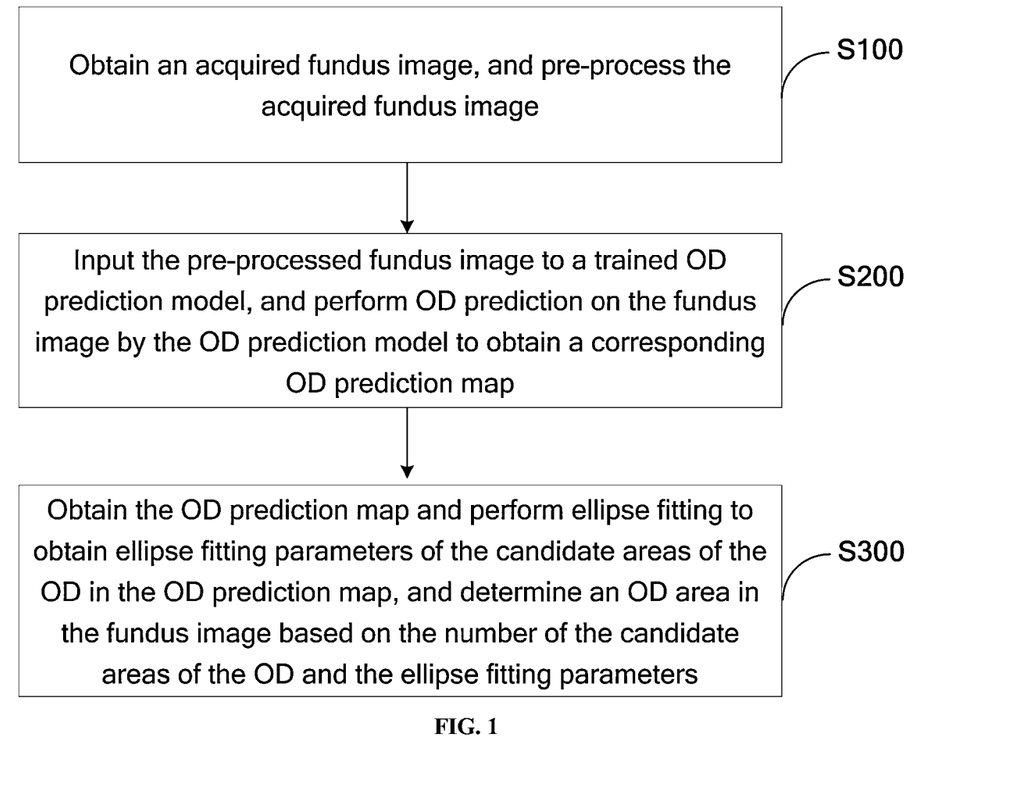
FIG. 1 is a flow chart of a method for recognizing a fundus image according to one embodiment of the present disclosure.

FIG. 1 shows a flow chart of a method for recognizing a fundus image according to one embodiment of the present disclosure. As shown in FIG. 1, the method includes: step S100, an acquired fundus image is obtained, and the acquired fundus image is pre-processed. Here, it should be pointed out that various equipment such as a desktop fundus camera or a handheld fundus camera may be used to acquire the fundus image, and other methods may also be used. The method for acquiring the fundus image is not limited here. At the same time, the method for pre-processing the acquired fundus image may include at least one of cropping, grayscale conversion, contrast-limited adaptive histogram equalization (CLAHE), γ correction, and normalization processing.

Step S200, the pre-processed fundus image is input to a trained OD prediction model, and OD prediction is performed on the fundus image by the OD prediction model to obtain a corresponding OD prediction map. It should be pointed out that when the trained OD prediction model is used for prediction and positioning of an OD in the fundus image, the imaging quality of the fundus image is not very high due to the influence of the shooting equipment and shooting methods, and light leakage, rainbow spots, and lens stains are likely to occur. Therefore, in the method for recognizing a fundus image of the embodiment of the present disclosure, when the trained OD prediction model is used for recognition and positioning of the OD in the fundus image, multiple candidate areas of the OD will be recognized for the fundus image with not very standard imaging quality. Each recognized candidate area of the OD will be marked in the OD prediction map.

Further, through step S300, the OD prediction map is obtained and ellipse fitting is performed on each candidate area of the OD in the OD prediction map to obtain ellipse fitting parameter of each candidate area of the OD in the OD prediction map, and an OD area in the fundus image is determined based on the number of the candidate areas of the OD and the ellipse fitting parameters.

Therefore, according to the method for recognizing a fundus image of the embodiment of the present disclosure, the trained OD prediction model is used for positioning of the OD in the fundus image, the candidate areas of the OD are first located in the fundus image, then ellipse fitting is performed on an image (namely, the OD prediction map) in which the candidate areas of the OD are located, and then the final OD area is determined according to the number of the candidate areas of the OD and the ellipse fitting parameters. Therefore, for the acquired fundus images with low imaging quality (that is, fundus images with light leakage, rainbow spots, and lens stains), multiple possible candidate areas of the OD can still be predicted from the fundus image by the OD prediction module, and then the final OD area is selected and determined from the multiple candidate areas of the OD by image post-processing, which not only realizes recognition and positioning of the OD area of the fundus image in various situations, but also effectively improves the accuracy of the positioning of the OD area.

According to the above, in the method for recognizing a fundus image of the embodiment of the present disclosure, when the prediction and positioning of the candidate areas of the OD in the fundus image are performed, the trained OD prediction model is used. Therefore, when the method of the embodiment of the present disclosure is performed, it is necessary to construct the OD prediction model first, and train the constructed OD prediction model.

In a possible implementation, the OD prediction model may adopt a deep learning model of Bi-directional ConvLSTM U-Net with Densely connected convolutions (BCDU-Net), improved U-Net. U-Net is a neural network model commonly used for semantic segmentation of medical images, which includes 4 up-sampling and 4 down-sampling processes. BCDU-Net adds a two-way convolutional long short-term memory network (LSTM) and a densely connected convolutional network to the basic U-Net, which makes the segmentation effect of the model better.

After the network model of the OD prediction model is determined, the OD prediction model can be trained. That is, by setting a corresponding model training module, the model training module trains and learns the OD prediction model. During model training, it is necessary to acquire a large number of fundus images and corresponding marked OD segmentation effect images as samples, so as to construct a training set and a test set respectively. The test set is also used as a verification set after each epoch of model training to select and save an optimal model.

At the same time, before using the fundus images in the above training set to train the OD prediction model, it is also necessary to perform pre-processing operations on the fundus images. In a possible implementation, the pre-processing operations on the fundus image sequentially include: reading the complete image (that is, the acquired color fundus image); cropping the black edges and retaining the fundus area; extracting the blue channel of the image as a grayscale image; and performing contrast-limited adaptive histogram equalization (CLAHE), γ correction, and normalization processing.

After being subjected to the above pre-processing operations, various sample can be input into the OD prediction model to train the OD prediction module. It should be pointed out that in the present disclosure, when model training is performed, unlike the commonly used cross entropy, DiceLoss is used as the loss function of the model, and a calculation formula is as follows:

$$DiceLoss(A, B) = 1 - Dice(A, B)$$

$$Dice(A, B) = \frac{2 \times \|A \cap B\|}{\|A\| + \|B\|}.$$

A and B represent the OD prediction map of the model and the marked OD segmentation effect image respectively, $\|A\|$ represent the area of the image A calculated in pixels, and represent $\|A \cap B\|$ the image of the intersection of the A and the B.

Figure 2:
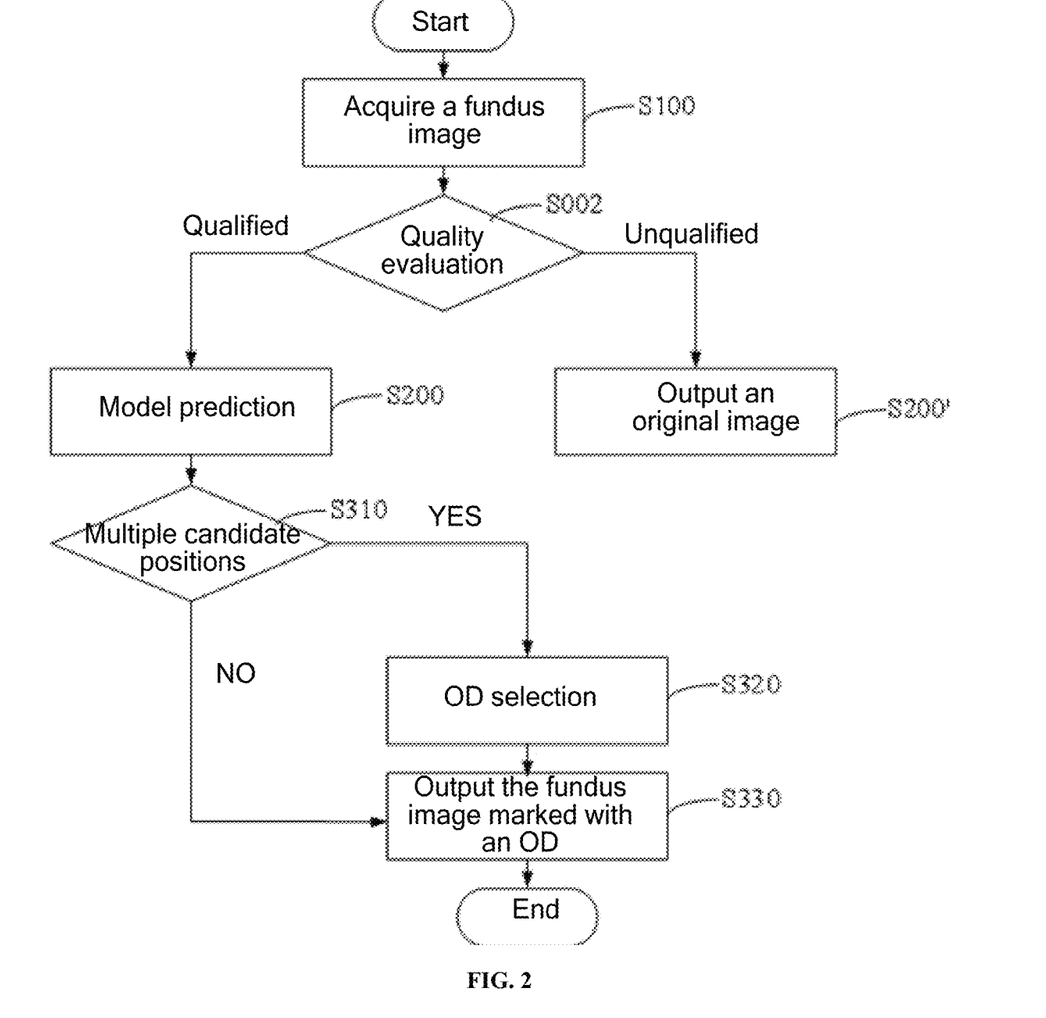
FIG. 2 is a flow chart of a method for recognizing a fundus image according to another embodiment of the present disclosure.

After the OD prediction model is trained and verified, that is, after the OD prediction model is trained and converges to the optimal, the OD of the fundus image can be recognized. Referring to FIG. 2, after the fundus image that currently needs to be recognized is acquired, the acquired fundus image is pre-processed. Here, it should be pointed out that the pre-processing operations on the fundus image may be the same pre-processing operations used for model training.

After pre-processing the fundus image and before inputting it to the OD prediction model for recognition of the OD, referring to FIG. 2, step S002 of evaluating the quality of the currently acquired fundus image may further be included.

Specifically, a two-class deep learning model may be used to evaluate the quality of the fundus image. That is, the two-class deep learning model is used to evaluate the quality of the pre-processed fundus image, and determine whether the fundus image is qualified. If it is qualified, it means that the OD area of the fundus image is visible, and the OD area can be recognized. If it is unqualified, it means that there is no OD area in the fundus image, or the OD area is blurred and invisible. Therefore, an original image is output through step S200' at this time, and the OD area is not recognized.

Here, those skilled in the art can understand that the quality evaluation of the fundus image mainly refers to determining whether the OD in the fundus image is visible, and the imaging quality of the fundus image (that is, whether there is light leakage, rainbow spots, and lens stains) does not need to be determined.

In the method for recognizing a fundus image of the embodiment of the present disclosure, the quality of the fundus image is first evaluated before inputting the pre-processed fundus image into the OD prediction model for prediction and positioning of the OD to ensure that the recognition and positioning of the OD area are performed on the premise that an OD is present in the fundus image, thereby avoiding the recognition of the fundus images with blurred OD or without OD, which also prevents unnecessary operations.

Further, after the quality of the fundus image is evaluated to be qualified (that is, the OD in the fundus image is visible), the pre-processed fundus image can be input to the OD prediction module for preliminary recognition and positioning of the OD area. In the method of the embodiment of the present disclosure, when the OD prediction model is used for recognition and positioning of the OD in the fundus image, the obtained OD prediction map is marked with all possible candidate areas of the OD.

That is to say, when the above OD prediction model is used for recognition and positioning of the OD in the fundus image, for the fundus images that may have abnormalities such as light leakage, rainbow spots, and/or lens stains, as long as the OD is present, the OD area can be recognized and determined. This also greatly reduces the requirements for the imaging quality of the fundus images, such that the method in the embodiment of the present disclosure can be applied to various fundus images.

Furthermore, after the qualified fundus image is input to the OD prediction model to obtain the OD prediction map, the OD prediction map can be post-processed to select and determine the final OD area from multiple candidate areas of the OD.

According to the above, when the final OD area is determined according to the OD prediction map, the following two situations are included.

One is that there is one candidate area of the OD marked in the OD prediction map, which corresponds to the acquired fundus image with high imaging quality, and there is no light leakage, rainbow spots, and/or lens stains. In this case, the candidate area of the OD marked in the OD prediction map can be directly used as the OD area, ellipse fitting can be performed on this area, and corresponding ellipse fitting parameters can be output.

The other is that there is more than one OD area marked in the OD prediction map. In this case, the acquired fundus images may have light leakage, rainbow spots, and/or lens stains. In this case, it is necessary to select the most matching area from more than one candidate areas of the OD as the OD area.

Therefore, referring to FIG. 2, in the method of the embodiment of the present disclosure, through step S200, the OD prediction model is used for positioning and recognition of the OD in the fundus image to obtain the corresponding OD prediction map, and then through step S310, it is determined whether there is only one candidate area of the OD marked in the OD prediction map. If not, through step S320, the final OD area is selected from the OD prediction map. If yes, step S330 is directly performed, the candidate area of the OD marked in the OD prediction map is used as the OD area, and the corresponding ellipse fitting parameters are output.

In a possible implementation, before step S310 of determining whether there is more than 1 candidate area of the OD in the OD prediction map is performed, the method further includes obtaining the OD prediction map and performing ellipse fitting to obtain the corresponding ellipse fitting parameters.

Figure 3:
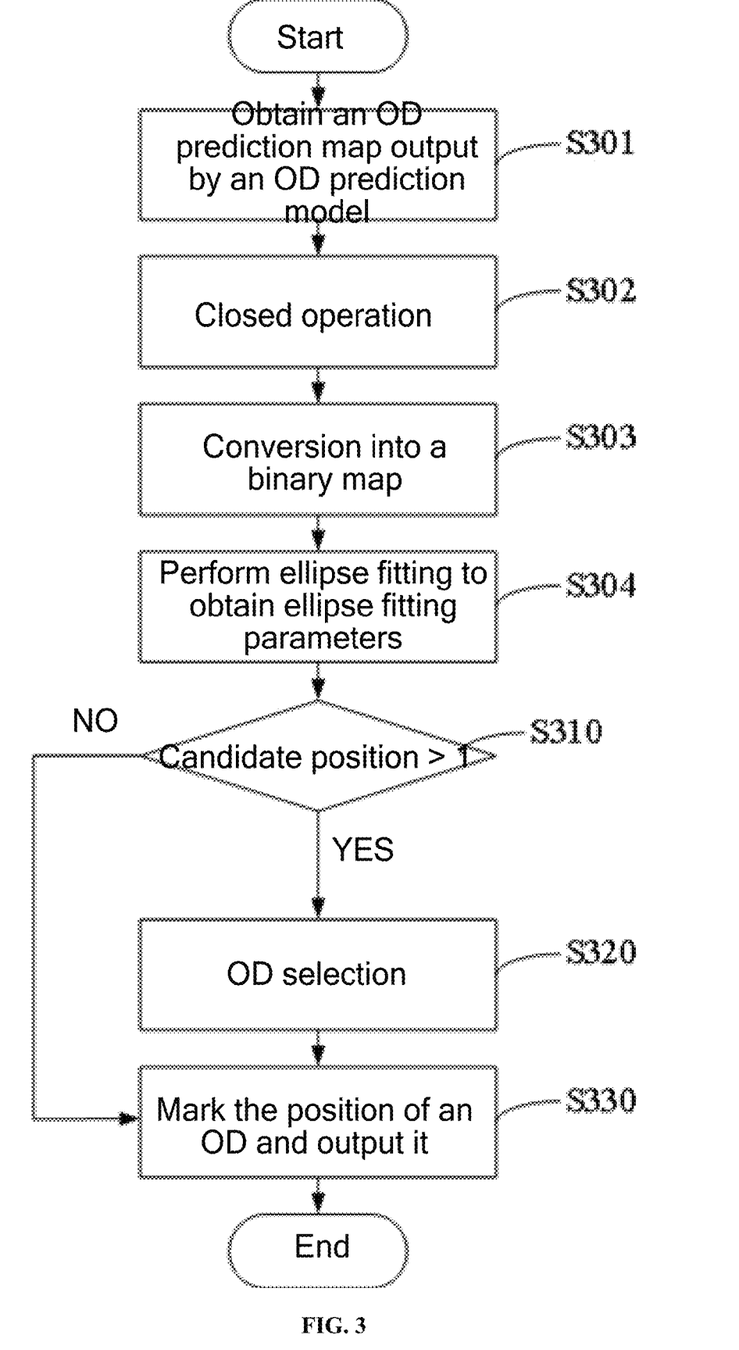
FIG. 3 is a flow chart of determining a final OD area from multiple candidate areas of an OD after the multiple candidate areas of the OD are recognized in a method for recognizing a fundus image according to one embodiment of the present disclosure.

That is, referring to FIG. 3, through step S301, after the output result of the OD prediction model is read to obtain the OD prediction map, firstly, step S302 of performing closed operation on the OD prediction map (first expansion and then erosion) is performed. Then step S303 of performing binarization processing on the OD prediction map (which is a grayscale image) and converting the OD prediction map into a binary map is performed. Then through step S304, ellipse fitting is performed on the candidate area of the OD in the binary map to obtain the corresponding ellipse.

Here, it should be pointed out that ellipse fitting is performed on each candidate area of the OD. Correspondingly, the obtained ellipse fitting parameters include the ellipse fitting parameters of each candidate area of the OD.

More specifically, when ellipse fitting is performed, the fitEllipse( ) function of OpenCV can be used. The general form of ellipse fitting is:

$$F(a; x) = A_{xx}x^2 + A_{xy}xy + A_{yy}y^2 + A_x x + A_y y + A_0.$$

a represents the ellipse fitting parameters to be solved:

$$a = [A_{xx}, A_{xy}, A_{yy}, A_x, A_y, A_0].$$

x represents all elliptic points to be fitted:

$$x(x_i, y_i), \text{ for } i=1 \ldots n.$$

This function uses an algebraic distance based on an L2 norm as an objective function to solve the ellipse fitting parameters.

According to the above, when there is only one candidate area of the OD, combined with the previous quality evaluation results, it can be determined that the candidate area is the OD area of the fundus image. At this time, the OD area can be directly marked at the corresponding position of the fundus image, and the corresponding ellipse fitting parameters and the marked fundus image are output.

When there is more than 1 candidate area of the OD, that is, through step S310, when it is determined that there is more than 1 candidate area of the OD, it is necessary to determine one optimal area from multiple candidate areas of the OD as the OD area of the fundus image.

In a possible implementation, selecting and determining the final OD area from two or more candidate areas of the OD may be determined based on the vascular pixels in the candidate area.

That is, first, according to the ellipse fitting parameters corresponding to each candidate area of the OD, a corresponding elliptic area is cropped from the OD prediction map. Then, edge detection is performed on the elliptic area to obtain a vascular pixel map of the candidate area of the OD. Furthermore, the number of vascular pixels in each vascular pixel map is calculated, and the final OD area is determined based on the number of vascular pixels.

When edge detection is performed on the elliptic area, a multi-level edge detection algorithm based on a Canny operator is used for detection.

Figure 4:
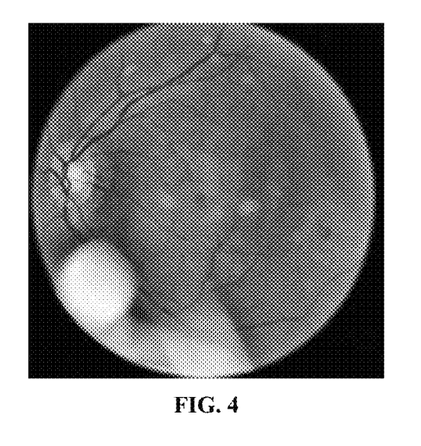
FIG. 4 is a fundus grayscale image obtained after pre-processing an acquired fundus image in a method for recognizing a fundus image according to one embodiment of the present disclosure.
Figure 5:
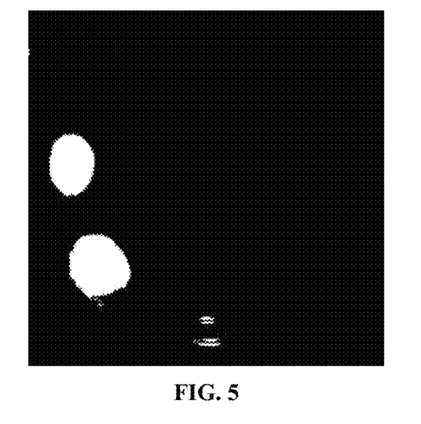
FIG. 5 is a fundus image of an OD prediction map obtained in a method for recognizing a fundus image according to one embodiment of the present disclosure.

More specifically, referring to FIG. 4, FIG. 5, FIG. 6, and FIG. 7, first, according to the ellipse fitting parameters obtained previously, the corresponding elliptic area is cropped from the OD prediction map (FIG. 4). In order to reduce the influence brought by the elliptic contour, in the method of the embodiment of the present disclosure, the elliptic contour is drawn as a background color (FIG. 5).

Figure 6:
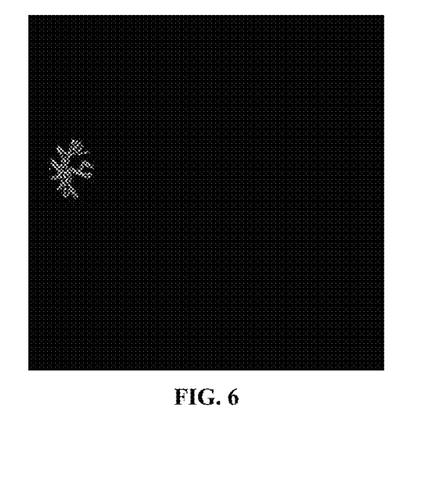
FIG. 6 is a diagram of a candidate area of an OD recognized in a method for recognizing a fundus image according to one embodiment of the present disclosure.
Figure 7:
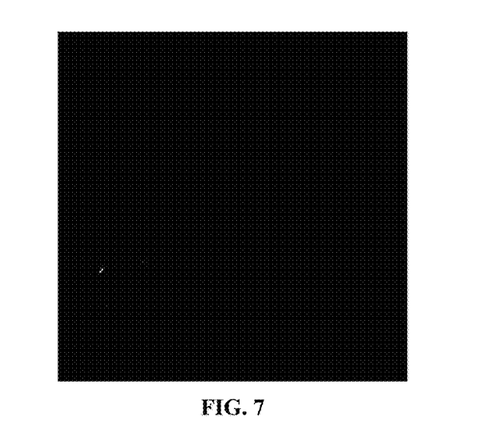
FIG. 7 is a diagram of another candidate area of an OD recognized in a method for recognizing a fundus image according to one embodiment of the present disclosure.

Then, for each candidate area of the OD, the Canny operator is used for edge detection to obtain the internal vascular pixel map of each candidate area of the OD (as shown in FIG. 6 and FIG. 7). The OD is the confluence of fundus blood vessels, and there are relatively few blood vessels in other areas. Therefore, by calculating the count of the vascular pixels in each area, the one with the largest count can be selected as the final OD area.

The multi-level edge detection algorithm based on the Canny operator includes the following main calculation steps.

First, Gaussian filtering is used to filter the candidate area of the OD to eliminate noise in the image.

Then, the gradient magnitude and direction of the candidate area of the OD are calculated. The convolution array used to calculate the x-axis direction is:

$$G_x = \begin{bmatrix} -1 & 0 & 1 \\ -2 & 0 & 2 \\ -1 & 0 & 1 \end{bmatrix}.$$

The convolution array in the y-axis direction is:

$$G_y = \begin{bmatrix} -1 & -2 & -1 \\ 0 & 0 & 0 \\ 1 & 2 & 1 \end{bmatrix}.$$

Then, the gradient amplitude is calculated by the following formula:

$$G = \sqrt{G_x^2 + G_y^2}.$$

The direction is:

$$\theta = \arctan\left(\frac{G_y}{G_x}\right).$$

Next, non-maximum suppression is performed on the candidate area of the OD to eliminate the influence of non-edge pixels.

Finally, the hysteresis threshold is used to filter pixel values to be retained.

Therefore, through the above preliminary recognition and positioning of the OD area in the fundus image by the OD prediction model, the OD prediction map marked with one or more candidate areas of the OD is obtained, and then post-processing is performed based on the OD prediction map. The final OD area is selected and determined from the OD prediction map, which effectively guarantees the accuracy of recognition and positioning of the OD. At the same time, for the fundus images with low imaging quality (that is, with abnormalities such as light leakage, rainbow spots, and lens stains), the OD area can still be accurately recognized, which effectively reduces the requirements for the imaging quality of the fundus images, and greatly reduces the difficulty of recognition of the OD.

Furthermore, the method of the embodiment of the present disclosure further includes a step of recognizing an OC. It should be pointed out that recognizing the OC needs to be performed based on the previously recognized OD. That is to say, after the OD area in the fundus image is located using any one of the above methods, a partial image of the OD with the located OD area as a center can be obtained, and the OC is recognized on the basis of the partial image of the OD.

In a possible implementation, when the OC is recognized, it is first necessary to pre-process the partial image of the OD with the OD as the center. Here, those skilled in the art can understand that the pre-processing operations on the partial image of the OD are the same as or similar to the pre-processing operations on the fundus image when the OD is recognized, so it will not be repeated here.

At the same time, when the corresponding partial image of the OD is obtained based on the recognition result of the OD obtained during the previous recognition of the OD, the partial image of the OD with a center of the OD as an image center can be cropped according to central coordinates of the OD output by the OD prediction model to be used as the region of interest during the recognition of the OC in the embodiment of the present disclosure.

In addition, in the embodiment of the present disclosure, when the OC is recognized, a deep learning method is also used to perform preliminary positioning of the candidate area of the OC. That is, OC prediction is performed on the obtained partial image of the OD by a trained OC prediction model to determine the candidate area of the OC in the partial image of the OD.

Those skilled in the art can understand that when the deep learning method is used to perform prediction and positioning of the candidate area of the OC, it is also necessary to train the constructed OC prediction model to make the constructed OC prediction model converge to the optimal network structure.

In addition, when the OC prediction model is trained, the used training samples are similar to those used during training of the OD prediction model, and sample images can also be pre-processed before the samples are input to the OC prediction model.

In the training process of the OC prediction model, the pre-processing on the sample image specifically includes the following steps: the sample image with black edges cropped is read, and according to the OD prediction model, the center of the OD is output, and the partial image of the OD with the center of the OD as the image center is cropped to be used as the region of interest. Then the image pre-processing operation method used for the training of the OD prediction model can be used for processing.

At the same time, it should also be noted that in the method of the embodiment of the present disclosure, when OC prediction is performed on the partial image of the OD by the trained OC prediction model to determine the candidate area of the OC, there may be one or more candidate areas of the OC. When there are two or more candidate areas of the OC, the candidate position closest to the center of the partial image of the OD is selected as the final candidate area of the OC.

After the candidate area of the OC is located from the partial image of the OD, ellipse fitting is performed on the candidate area of the OC, and a relationship between a boundary of the candidate area of the OC and the OD area is determined according to fitting results. Specifically, referring to FIG. 8, through step S400, the partial image of the OD is obtained, and through step S500, OC prediction is performed on the partial image of the OD by the OC prediction model to determine the corresponding candidate area of the OC, and then through step S600, it is detected whether the boundary of the determined candidate area of the OC exceeds the OD area. When it is detected that the boundary of the candidate area of the OC exceeds the OD area, step S700 of adjusting the candidate area of the OC until the candidate area of the OC is adjusted within the OD area so as to determine the position of the OC is performed. When it is detected that the boundary of the candidate area of the OC does not exceed the OD area, it can be determined that the candidate area of the OC is the position of the OD. Therefore, step S800 of marking the position of the OC in the partial image of the OD according to the determined candidate area of the OC can be directly performed.

Figure 8:
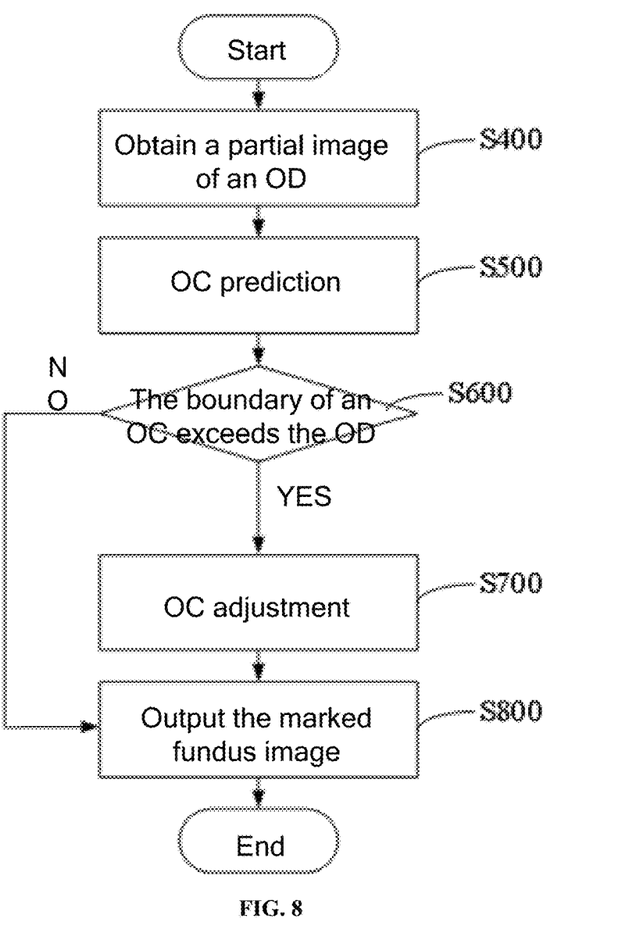
FIG. 8 is a flow chart of recognizing an OC in a method for recognizing a fundus image according to one embodiment of the present disclosure.

In a possible implementation, in step S700, when the candidate area of the OC is adjusted, the mask Otsu threshold method can be used to adjust the candidate area of the OC by using the partial image of the OD as a mask.

Figure 9:
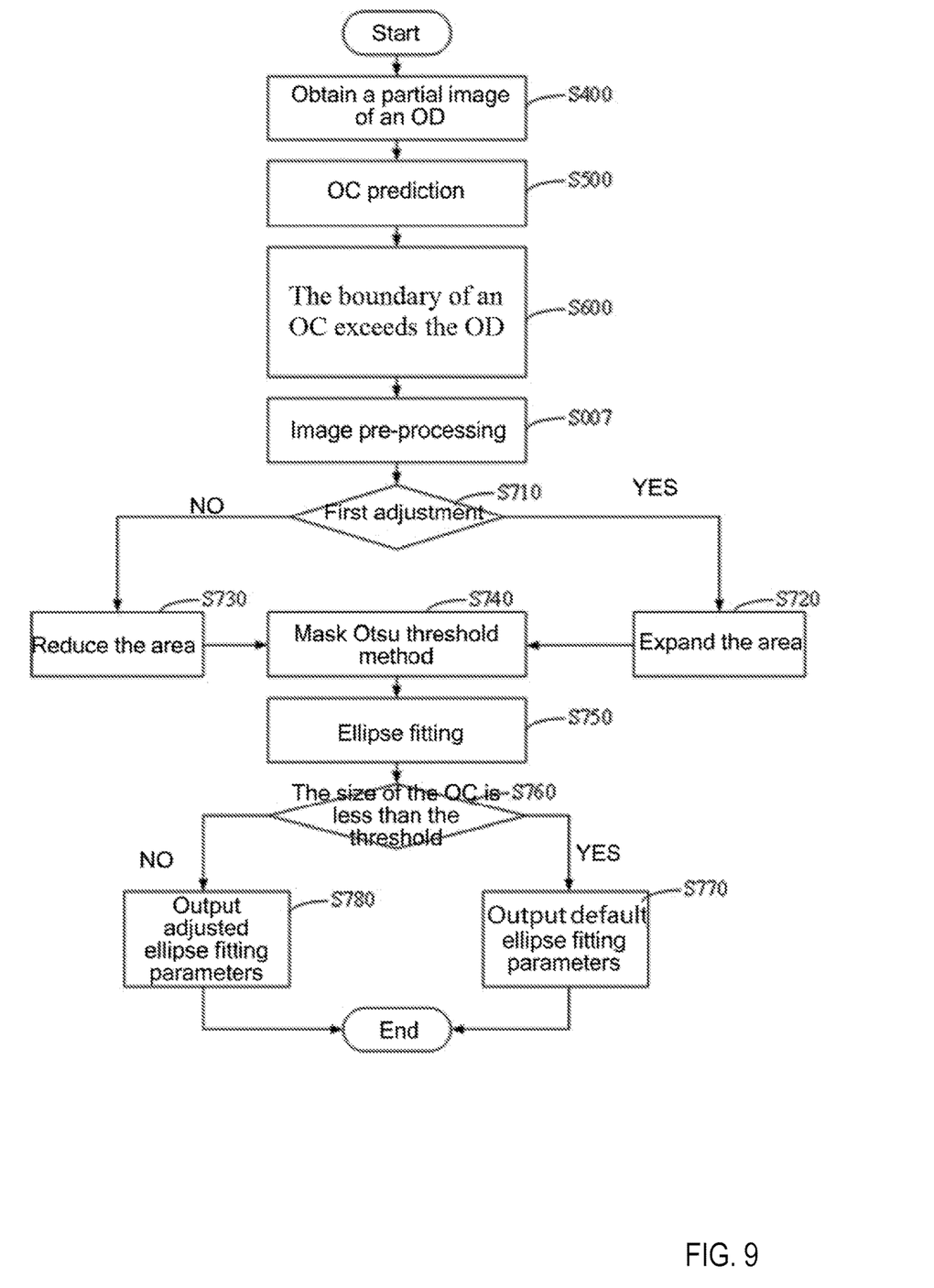
FIG. 9 is a flow chart of adjusting a candidate area of an OC in the process of recognizing the OC in a method for recognizing a fundus image according to one embodiment of the present disclosure.

Specifically, referring to FIG. 9, before the adjustment of the OC, the method further includes step S007, a step of pre-processing the image. Here, it should be pointed out that the pre-processing operations on the partial image of the OD include Gaussian filtering and grayscale conversion.

Further, in a possible implementation, during the adjustment of the OC, step S710 may be performed first to determine whether the current adjustment is the first adjustment. If it is the first adjustment, step S720 of expanding the candidate area of the OC, and then using the expanded candidate area of the OC as the candidate area of the OC to be adjusted is performed.

During expansion processing, the maximum size of the ellipse fitting parameters is calculated first, and then the maximum value is used as an initial value to expand a preset pixel value (for example: 30 pixels) outward as the adjusted candidate area of the OC. Here, it should be pointed out that the preset pixel value during the expansion processing can be flexibly set according to the actual situation. For example, the preset pixel value has a range of 20-40. If it is not the first adjustment (that is, it is still out of bounds after the first adjustment), step S730 is required to reduce the candidate area of the OC, and use the reduced candidate area of the OC as the candidate area of the OC to be adjusted. During reduction processing of the candidate area of the OC, the operation mode is the same or similar to the expansion mode, and will not be repeated here.

After the candidate area of the OC is expanded or reduced, the expanded or reduced candidate area of the OC can be used as a mask, and then the mask Otsu threshold method is applied on the partial image of the OD to adjust the position of the candidate area of the OD.

A process of applying the mask Otsu threshold method to adjust the position of the candidate area of the OD specifically includes the following steps.

The partial image of the OD in the mask part is obtained, and the histogram of the partial image of the OD and the global average gray scale are calculated.

The value of a binarization threshold t is set to 1-254, the threshold t is traversed in turn, the foreground and the background are distinguished according to the threshold t, and the between-class variance between the two parts is calculated.

A calculation formula is:

$$Var(t) = C_f \bullet (L_f - L_{all})^2 + C_b \bullet (L_b - L_{all})^2$$

Var(t) represents the between-class variance, Cf and Lf represent the proportion of foreground pixels and the average gray scale respectively, Cb and Lb represent the proportion of background pixels and the average gray scale respectively, and Lall represents the global average gray scale.

According to the maximum between-class variance, an optimal threshold is determined from the above preset binarization thresholds. That is, t that maximizes the between-class variance is the optimal binarization threshold output by the algorithm.

According to the determined optimal binarization threshold, binarization processing is performed on the current candidate area of the OC (that is, the candidate area of the OC after the expansion or reduction processing) in the partial image of the OD, and then through step S750, ellipse fitting is performed to obtain the size of the OC. Then, step S760 of determining whether the currently obtained size of the OC is less than the preset size of the OC is performed. When it is determined that the currently obtained size of the OC is less than the preset size of the OC, step S770 of outputting the default ellipse fitting parameters is directly performed. When it is determined that the currently obtained size of the OC is greater than or equal to the preset size of the OC, step S780 of outputting the adjusted ellipse fitting parameters is performed.

After the current adjustment of the candidate area of the OC is completed through the above steps, step S600 of determining whether the boundary of the candidate area of the OC after adjustment exceeds the OD area is performed again. If it still exceeds the OD area, the above steps are repeated and the candidate area of the OC is continued to be adjusted. The adjustment method will not be repeated here. If it no longer exceeds the OD area, it indicates that the adjusted candidate area of the OC at this time conforms to medical common sense. The adjusted candidate area of the OC can be used as the final OC area, so the ellipse fitting parameters obtained after the ellipse fitting is performed on the adjusted candidate area of the OC can be directly output, and the marked fundus image is returned, thereby completing the recognition of the OD and the OC of the fundus image.

Therefore, in the method for recognizing a fundus image of the embodiment of the present disclosure, after the OD area in the fundus image is recognized and located, the OC area is recognized. During the recognition of the OC area, the candidate area of the OC is adjusted by the relationship between the predicted boundary of the candidate area of the OC and the OD area, so as to ensure the accuracy of the finally recognized OC area.

In addition, in the process of adjusting the OC, the threshold value during binarization processing on the partial image of the OD is determined according to the mask Otsu threshold method, so as to effectively ensure the timeliness of the algorithm while ensuring the accuracy of the recognized OC.

Furthermore, after the ellipse fitting parameters of the OD area (that is, the OD fitting parameters) and the ellipse fitting parameters of the OC area (that is, the OC fitting parameters) are respectively obtained in the above manner, the longitudinal diameter of the OD and the longitudinal diameter of the OC can be calculated respectively according to the obtained OD fitting parameters and OC fitting parameters. Furthermore, a ratio of the longitudinal diameter of the OD to the longitudinal diameter of the OC is calculated to obtain a longitudinal cup-to-disc ratio. Then, according to the calculated longitudinal cup-to-disc ratio, it is determined whether the OD area of the currently recognized fundus image is abnormal.

Correspondingly, based on any one of the above methods for recognizing a fundus image, the present disclosure further provides a device for recognizing a fundus image. Since the working principle of the device for recognizing a fundus image provided by the present disclosure is the same as or similar to the principle of the method for recognizing a fundus image provided by the present disclosure, the repetition will not be repeated.

Figure 10:
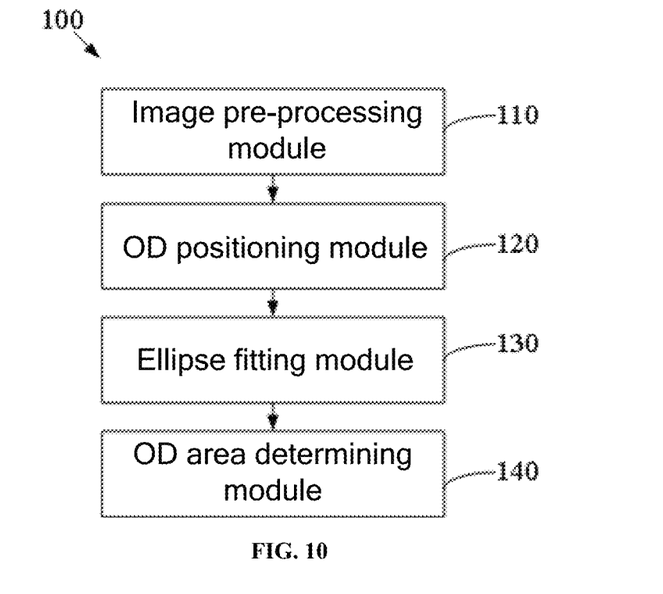
FIG. 10 is a structural block diagram of a device for recognizing a fundus image according to one embodiment of the present disclosure.

Referring to FIG. 10, the device 100 for recognizing a fundus image provided by the present disclosure includes an image pre-processing module 110, an OD positioning module 120, an ellipse fitting module 130, and an OD area determining module 140. The image pre-processing module 110 is configured to obtain an acquired fundus image, and pre-process the acquired fundus image. The OD positioning module 120 is configured to input the pre-processed fundus image to a trained OD prediction model, and perform OD prediction on the fundus image by the OD prediction model to obtain a corresponding OD prediction map. The OD prediction map is marked with one or more located candidate areas of the OD. The ellipse fitting module 130 is configured to obtain the OD prediction map and perform ellipse fitting to obtain ellipse fitting parameters of the candidate areas of the OD in the OD prediction map. The OD area determining module 140 is configured to determine an OD area in the fundus image based on the number of the candidate areas of the OD and the ellipse fitting parameters.

In addition, it should also be pointed out that in the device 100 for recognizing a fundus image of the embodiment of the present disclosure, the trained OD prediction model is used during the OD prediction of the fundus image. That is, a neural network is used to predict candidate areas of the OD. Therefore, the device of the embodiment of the present disclosure further includes a model training module. The model training module is used to train the OD prediction model, such that the OD prediction model converges to an optimal network structure. Here, it should also be pointed out that the model training module is also used to train an OC prediction model, such that the OC prediction model converges to an optimal network structure.

At the same time, it should also be pointed out that in a possible implementation, the device of the embodiment of the present disclosure is mainly divided into four parts, one part including the aforementioned four modules of the image pre-processing module 110, OD positioning module 120, ellipse fitting module 130, and the OD area determining module 140 to realize an OD positioning and selecting unit (not shown in the figure), one part of a training unit (not shown in the figure) including the model training module, one part of an OC positioning and selecting unit (not shown in the figure) for OC prediction and adjustment, and an index quantification module (not shown in the figure) for determining whether the OD area of the fundus image is abnormal according to OD fitting parameters and OC fitting parameters.

The above device 100 for recognizing a fundus image is used to recognize the OD and the OC of the fundus image. In the process of recognizing the OD, the trained OD prediction model is used to predict the candidate area of the OD first, and then the final OD area is selected from the candidate area of the OD by the designed method based on the vascular pixel count in the OD area, which not only effectively improves the accuracy of the OD detection and recognition results, but also achieves the effect of improving the timeliness of the algorithm. In the process of recognizing the OC, according to the predicted relationship between the boundary of the candidate area of the OC and the OD area, the candidate area of the OC is adjusted to ensure the accuracy of the final recognition and positioning of the OC area. In addition, when the OC is adjusted, the threshold for image binarization processing is determined by the designed mask Otsu threshold method, which not only ensures the accuracy of the detection results, but also further improves the timeliness of the algorithm.

Figure 11:
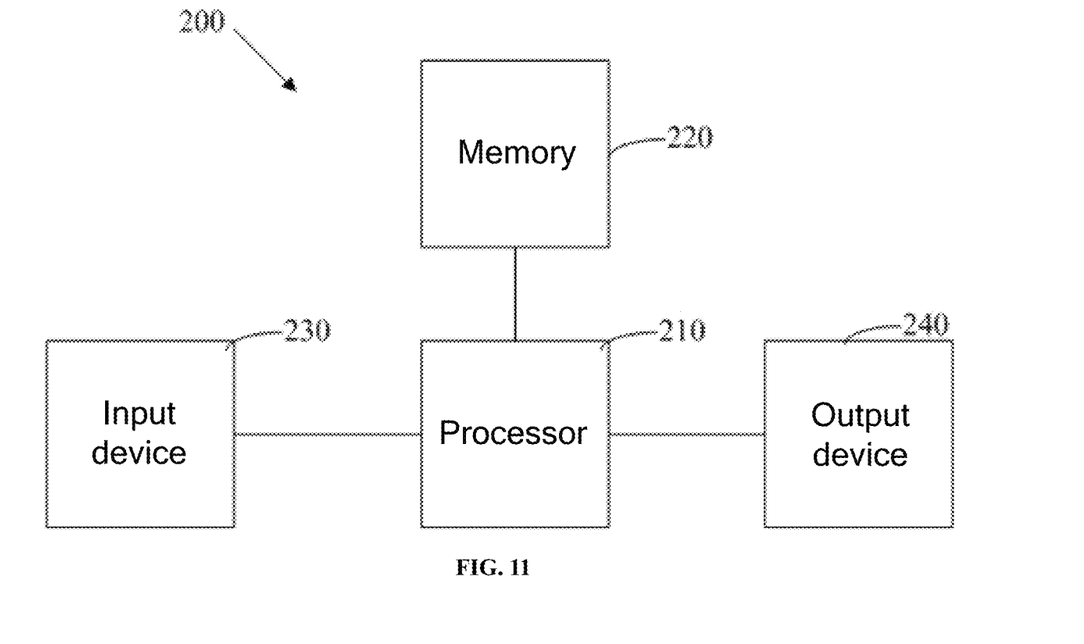
FIG. 11 is a structural block diagram of equipment for recognizing an OD in a fundus image according to one embodiment of the present disclosure.

Furthermore, according to another aspect of the present disclosure, equipment 200 for recognizing a fundus image is further provided. Referring to FIG. 11, the equipment 200 for recognizing a fundus image of the embodiment of the present disclosure includes a processor 210 and a memory 220 configured to store an instruction executable by the processor 210. The processor 210 is configured to implement any one of the above methods for recognizing a fundus image when executing the executable instruction.

Here, it should be pointed out that there may be one or more processors 210. At the same time, the equipment 200 for recognizing a fundus image of the embodiment of the present disclosure may further include an input device 230 and an output device 240. The processor 210, the memory 220, the input device 230, and the output device 240 may be connected through a bus or may be connected in other ways, which is not specifically limited here.

As a computer-readable storage medium, the memory 220 can be used to store software programs, computer-executable programs, and various modules, such as programs or modules corresponding to the method for recognizing a fundus image of the embodiment of the present disclosure. The processor 210 executes various functional applications and data processing of the equipment 200 for recognizing a fundus image by running a software program or module stored in the memory 220.

The input device 230 can be used to receive an input digital or signal. The signal may be a key signal related to user settings and function control of the device/terminal/server. The output device 240 may include display equipment such as a display screen.

The embodiments are described herein in a progressive manner. Each embodiment focuses on the difference from other embodiments, and the same and similar parts between the embodiments may refer to each other.

Specific examples are used herein to explain the principles and implementations of the present disclosure. The foregoing description of the embodiments is merely intended to help understand the method of the present disclosure and its core ideas; besides, various modifications may be made by a person of ordinary skill in the art to specific implementations and the scope of application in accordance with the ideas of the present disclosure. In conclusion, the content of this specification shall not be construed as a limitation to the present disclosure.

What is claimed is:

1. A method for recognizing a fundus image, comprising:
    obtaining an acquired fundus image, and pre-processing the acquired fundus image;
    inputting the pre-processed fundus image to a trained optic disc (OD) prediction model, and performing OD prediction on the fundus image by the OD prediction model to obtain a corresponding OD prediction map, wherein the OD prediction map is marked with one or more candidate areas of an OD; and
    obtaining the OD prediction map and performing ellipse fitting to obtain ellipse fitting parameters corresponding to each of the one or more candidate areas of the OD in the OD prediction map, and determining an OD area in the fundus image based on a number of the one or more candidate areas of the OD and the ellipse fitting parameters,
    wherein the method further comprises a step of recognizing an optic cup (OC):
    obtaining a partial image of the OD with a center of the OD as an image center, inputting the partial image of the OD into a trained OC prediction model, and performing OC prediction on the partial image of the OD by the OC prediction model to obtain a candidate area of the OC;
    performing ellipse fitting on the candidate area of the OC, and determining a relationship between a boundary of the candidate area of the OC and the OD area according to fitting results; and
    when it is determined that the boundary of the candidate area of the OC exceeds the OD area, adjusting the candidate area of the OC until the adjusted candidate area of the OC is within the OD area so as to determine the position of the OC; and a process of determining an OD area in the fundus image based on the number of the one or more candidate areas of the OD and the ellipse fitting parameters comprises:
when there are two or more candidate areas of the OD, according to the ellipse fitting parameters corresponding to each of the two or more candidate areas of the OD, cropping a corresponding elliptic area from the OD prediction map;
performing edge detection on each elliptic area to obtain a vascular pixel map corresponding to each of the two or more candidate areas of the OD; and
calculating a number of vascular pixels in each vascular pixel map, and determining a final OD area according to the number of vascular pixels.

2. The method according to claim 1, wherein a process of determining the final OD area according to the number of vascular pixels comprises:
selecting a candidate area of the OD with the largest number of vascular pixels as the OD area.

3. The method according to claim 1, wherein when edge detection is performed on each elliptic area, a multi-level edge detection algorithm based on a Canny operator is used for detection.

4. The method according to claim 1, wherein a process of obtaining the OD prediction map and performing ellipse fitting comprises:
performing binarization processing on the OD prediction map, and converting the OD prediction map into a binary map, and
performing the ellipse fitting on the one or more candidate areas of the OD in the binary map to obtain the corresponding ellipse fitting parameters.

5. The method according to claim 1, wherein when the candidate area of the OC is adjusted, the mask Otsu threshold method is used to adjust the candidate area of the OC by using the partial image of the OD as a mask.

6. The method according to claim 5, wherein when the candidate area of the OC is adjusted, the method further comprises:
determining whether the current adjustment is the first adjustment;
when the current adjustment is the first adjustment, expanding the candidate area of the OC as the candidate area of the OC to be adjusted; and
when the current adjustment is not the first adjustment, reducing the candidate area of the OC as the candidate area of the OC to be adjusted.

7. Equipment for recognizing an OD in a fundus image, comprising:
a processor; and
a memory, configured to store an instruction executable by the processor,
wherein the processor is configured to implement a method for recognizing the fundus image when executing the executable instruction; and wherein
the method comprises:
obtaining an acquired fundus image, and pre-processing the acquired fundus image;
inputting the pre-processed fundus image to a trained optic disc (OD) prediction model, and performing OD prediction on the fundus image by the OD prediction model to obtain a corresponding OD prediction map, wherein the OD prediction map is marked with one or more candidate areas of an OD; and
obtaining the OD prediction map and performing ellipse fitting to obtain ellipse fitting parameters corresponding to each of the one or more candidate areas of the OD in the OD prediction map, and determining an OD area in the fundus image based on a number of the one or more candidate areas of the OD and the ellipse fitting parameters,
wherein the method further comprises a step of recognizing an optic cup (OC):
obtaining a partial image of the OD with a center of the OD as an image center, inputting the partial image of the OD into a trained OC prediction model, and performing OC prediction on the partial image of the OD by the OC prediction model to obtain a candidate area of the OC;
performing ellipse fitting on the candidate area of the OC, and determining a relationship between a boundary of the candidate area of the OC and the OD area according to fitting results; and
when it is determined that the boundary of the candidate area of the OC exceeds the OD area, adjusting the candidate area of the OC until the adjusted candidate area of the OC is within the OD area so as to determine the position of the OC; and
a process of determining an OD area in the fundus image based on the number of the one or more candidate areas of the OD and the ellipse fitting parameters comprises:
when there are two or more candidate areas of the OD, according to the ellipse fitting parameters corresponding to each of the two or more candidate areas of the OD, cropping a corresponding elliptic area from the OD prediction map;
performing edge detection on each elliptic area to obtain a vascular pixel map corresponding to each of the two or more candidate areas of the OD; and
calculating a number of vascular pixels in each vascular pixel map, and determining a final OD area according to the number of vascular pixels.

8. The equipment for recognizing an OD in a fundus image according to claim 7, wherein a process of determining the final OD area according to the number of vascular pixels comprises:
selecting a candidate area of the OD with the largest number of vascular pixels as the OD area.

9. The equipment for recognizing an OD in a fundus image according to claim 7, wherein when the edge detection is performed on each elliptic area, a multi-level edge detection algorithm based on a Canny operator is used for detection.

10. The equipment for recognizing an OD in a fundus image according to claim 7, wherein a process of obtaining the OD prediction map and performing ellipse fitting comprises:
performing binarization processing on the OD prediction map, and converting the OD prediction map into a binary map, and
performing the ellipse fitting on the one or more candidate areas of the OD in the binary map to obtain the corresponding ellipse fitting parameters.

11. The equipment for recognizing an OD in a fundus image according to claim 7, wherein when the candidate area of the OC is adjusted, the mask Otsu threshold method is used to adjust the candidate area of the OC by using the partial image of the OD as a mask.

12. The equipment for recognizing an OD in a fundus image according to claim 11, wherein when the candidate area of the OC is adjusted, the method further comprises:
determining whether the current adjustment is the first adjustment;

when the current adjustment is the first adjustment, expanding the candidate area of the OC as the candidate area of the OC to be adjusted; and when the current adjustment is not the first adjustment, reducing the candidate area of the OC as the candidate area of the OC to be adjusted.

\* \* \* \* \*